(12) United States Patent
Itoh

(10) Patent No.: US 7,207,241 B2
(45) Date of Patent: Apr. 24, 2007

(54) CAP REMOVING APPARATUS

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 180 days.

(21) Appl. No.: 11/111,770

(22) Filed: Apr. 22, 2005

(65) Prior Publication Data

US 2007/0000352 A1   Jan. 4, 2007

(30) Foreign Application Priority Data

Apr. 26, 2004   (JP) .............................. 2004-129779

(51) Int. Cl.
B67B 7/00 (2006.01)
B67B 7/16 (2006.01)

(52) U.S. Cl. ........................................ 81/3.2; 53/381.4

(58) Field of Classification Search ................. 81/3.2, 81/3.36, 3.4, 3.55, 3.27; 53/381.4; 215/302; 220/274
See application file for complete search history.

(56) References Cited

U.S. PATENT DOCUMENTS 4,320,914 A * 3/1982 Simon ..................... 294/82.28

2005/0252342 A1* 11/2005 Itoh .............................. 81/3.2

FOREIGN PATENT DOCUMENTS

JP          05-221488      *  8/1993
JP          2731729        * 12/1997

* cited by examiner

*Primary Examiner*—Lee D. Wilson
*Assistant Examiner*—Robert Scruggs
(74) *Attorney, Agent, or Firm*—Nixon & Vanderhye, P.C.

(57) ABSTRACT

A cap removing apparatus includes a transfer path through which a container closed by a cap is transferred, a rotary driving mechanism provided in a first position and rotates the container, a correcting mechanism which corrects the posture of a knob of the cap, and a cap-removing mechanism which is provided in a second position, pinches the knob and removes the cap. A movable body, configured to move forward and backward between the first position and the second position, is provided on the transfer path. The movable body has a clamping mechanism. The clamping mechanism clamps the container with the cap whose knob has been posture-corrected in the first position, and moves the container from the first position to the second position. The clamping mechanism releases the clamping state at a time when the removal of the cap is completed, and returns to the first position.

3 Claims, 6 Drawing Sheets

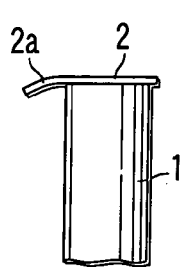 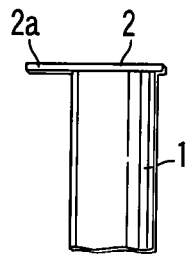 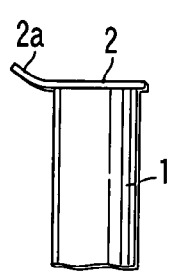 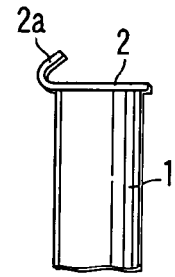
FIG. 6A  FIG. 6B  FIG. 6C  FIG. 6D
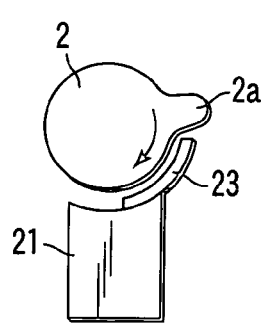 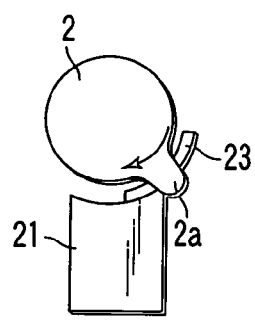 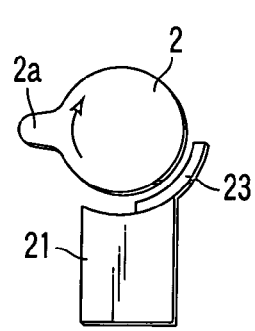 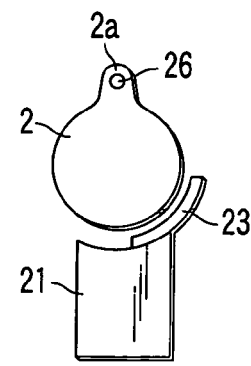
FIG. 7A  FIG. 7B  FIG. 7C  FIG. 7D
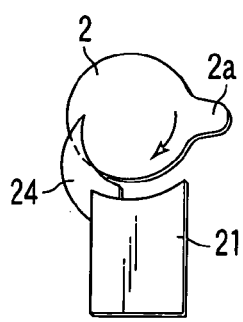 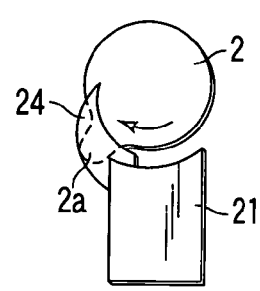 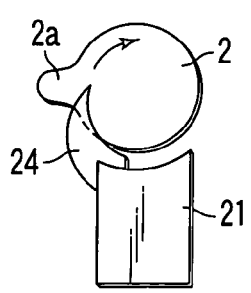 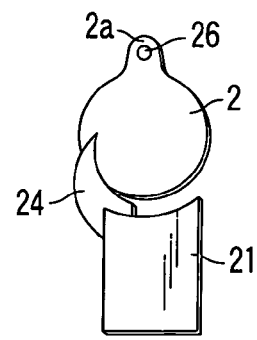
FIG. 8A  FIG. 8B  FIG. 8C  FIG. 8D

CAP REMOVING APPARATUS

CROSS-REFERENCE TO RELATED APPLICATIONS

This application is based upon and claims the benefit of priority from prior Japanese Patent Application No. 2004-129779, filed Apr. 26, 2004, the entire contents of which are incorporated herein by reference.

BACKGROUND OF THE INVENTION

1. Field of the Invention

The present invention relates to a cap removing apparatus, which corrects the posture of a knob of a cap that closes an opening end of a container, such as a test tube containing a sample, and thereafter removes the cap from the container.

2. Description of the Related Art

A conventional cap removing apparatus, disclosed in Japanese Patent No. 2731729, automatically removes a cap from an opening end of a test tube. This conventional cap removing apparatus comprises a test tube holder, a belt conveyor, a rotary driving mechanism, a correcting mechanism and a cap-removing mechanism.

The test tube holder holds a test tube with its opening end closed by a cap, so that the test tube is rotatable in a circumferential direction. The belt conveyor conveys the test tube held in the test tube holder. The belt conveyor has a tube-positioning position and a cap-removing position, which is provided at a predetermined distance from the tube-positioning position.

The rotary driving mechanism is provided in the tube-positioning position. The rotary driving mechanism rotates the test tube held in the test tube holder in the circumferential direction. The correcting mechanism corrects the position of the test tube rotated by the rotary driving mechanism, and corrects the posture of the knob of the cap, which has closed the opening end of the test tube.

The cap-removing mechanism is provided in the cap-removing position. The cap-removing mechanism pinches the knob of the cap whose posture has been corrected by the correcting mechanism, and removes the cap from the test tube. As a result, the opening end of the test tube is opened.

In the conventional cap removing apparatus described above, the test tube, the position of which has been corrected at the tube-positioning position, is conveyed together with the test tube holder to the cap-removing position by the belt conveyor. The cap, which has closed the opening end of the test tube, is removed from the test tube by the cap-removing mechanism in the cap removing position.

The test tube may circumferentially rotate while it is being transferred from the tube-positioning position to the cap-removing position. Accordingly, the knob of the cap may be deviated from the predetermined position at which the cap can be removed from the test tube in the tube-positioning position. In this case, therefore, in the conventional cap removing apparatus, the cap-removing mechanism cannot pinch the knob of the cap.

Further, in the conventional cap removing apparatus, the test tube is conveyed from the tube-positioning position to the cap-removing position by the belt conveyor, which is intermittently operated. Therefore, a time period between correcting the posture of the cap and removing the cap from the test tube is liable to be long.

BRIEF SUMMARY OF THE INVENTION

An object of the present invention is to provide a cap removing apparatus, which can successfully remove a cap from a container.

A cap removing apparatus according to an aspect of the present invention comprises: a transfer path, which has a first position and a second position that is provided at a predetermined distance from the first position, and which transfers a container closed by a cap having a knob, at least a part of the container being tube-like; a rotary driving mechanism, which is provided in the first position and rotates the container in a circumferential direction; a correcting mechanism which corrects posture of the knob; and a cap-removing mechanism, which is provided in the second position, pinches the knob whose posture has been corrected by the correcting mechanism, and removes the cap from the container. A movable body, which is configured to move forward and backward between the first position and the second position along the transfer path, is provided on the transfer path, the movable body having a clamping mechanism. The clamping mechanism clamps the container with the knob whose protrusion has been posture-corrected in the first position, moves the container from the first position to the second position by forward movement of the movable body while keeping the container in a clamping state. The clamping mechanism maintains the clamping state until removal of the cap from the container is completed, releases the clamping state at a time when the removal of the cap is completed, and returns to the first position by backward movement of the movable body.

In the cap removing apparatus according to the above aspect, the movable body, which is configured to move forward and backward between the first position and the second position along the transfer path, is provided on the transfer path. The movable body has the clamping mechanism, which clamps the container. The clamping mechanism moves the container from the first position to the second position by forward movement of the movable body.

With the apparatus described above, after correction of the posture of the knob, the container can be moved from the first position to the second position without changing the direction of the knob. Thus, the cap can be successfully removed from the container at the second position.

Moreover, in the cap removing apparatus according to the above aspect, an operation between correcting the posture of the knob of the cap and removing the cap from the container is speeded up as compared to that in the conventional cap removing apparatus using a belt conveyor.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 6A to 6D are side views, each showing a test tube transferred through a transfer path; FIG. 6A is a side view of a test tube with a cap having a knob bent downward relative to the horizontal, FIG. 6B is a side view of a test tube with a cap having a knob projecting horizontally, FIG. 6C is a side view of a test tube with a cap having a knob bent upward at an obtuse angle relative to the horizontal, and FIG. 6D is a side view of a test tube with a cap having a knob folded upward at an acute angle relative to the horizontal;

FIGS. 7A to 7D are plan views showing, in sequence along a direction of rotation of the cap, steps of correcting the posture of the knob of the cap by means of a lower correcting claw; and FIGS. 8A to 8D are plan views showing, in sequence along a direction of rotation of the cap, steps of correcting the posture of the knob of the cap by means of an upper correcting claw.

DETAILED DESCRIPTION OF THE INVENTION

Figure 1:
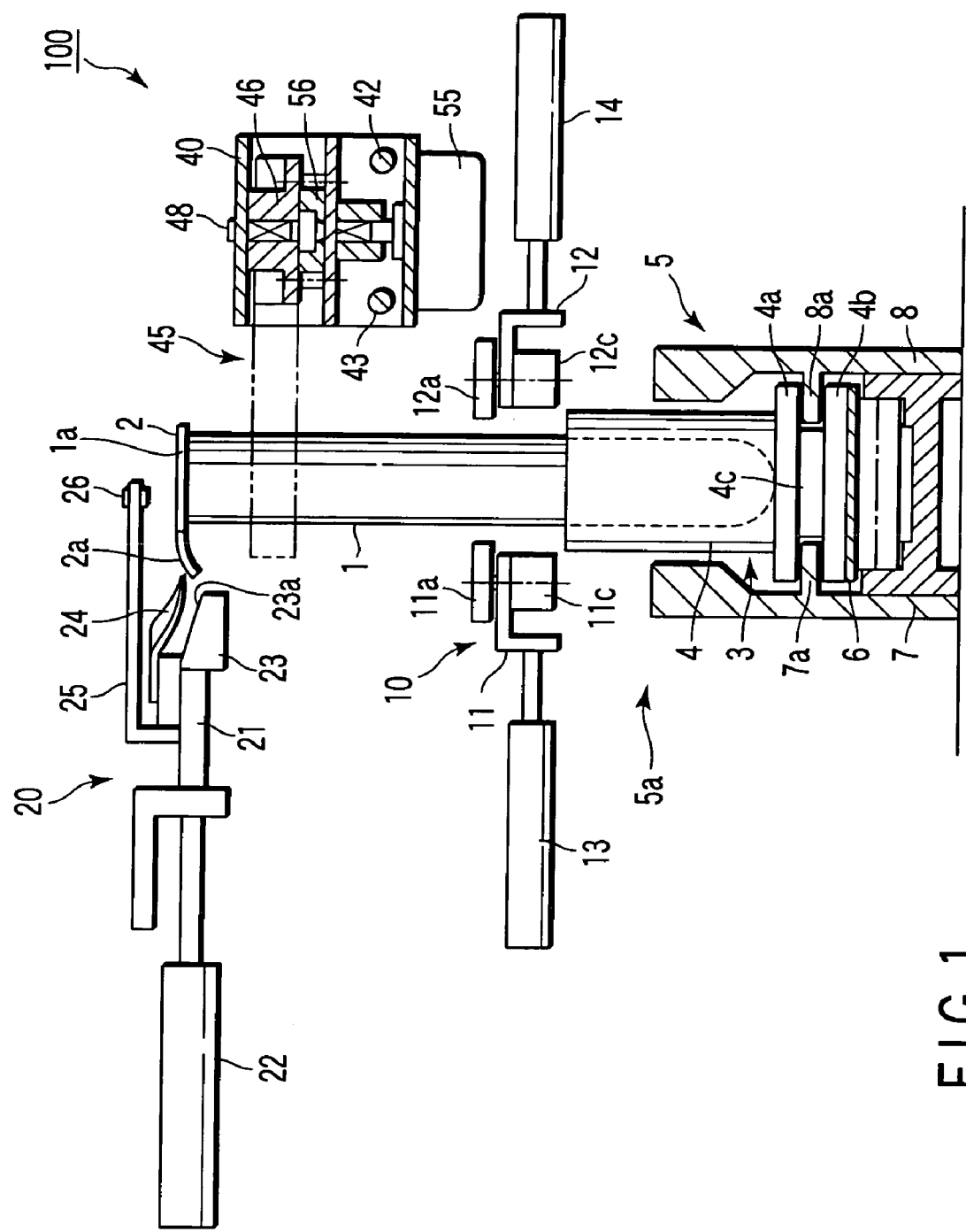
FIG. 1 is a sectional view showing a part of a cap removing apparatus according to an embodiment of the present invention.

A cap removing apparatus 100 according to an embodiment of the present invention will be described with reference to the accompanying drawings.

In the drawings, a reference numeral 1 denotes a test tube. The test tube 1 is, for example, a container, at least a part of which is tube-like. The test tube 1 contains a sample, such as blood. The test tube 1 has an opening end 1a. The opening end 1a of the test tube 1 is closed by a cap 2, which is removable. The cap 2 is held to the opening end 1a of the test tube 1 by, for example, adhesive force. The peripheral portion of the cap 2 has a knob 2a, which is used when the cap 2 is to be removed from the test tube 1.

The test tube 1 is intermittently transferred in a predetermined direction through a transfer path 5 in a state where it is held in a vertical position by a test tube holder 3, which serves as a holding mechanism. As shown in FIG. 1, the test tube holder 3 has a cylindrical portion 4 in which the test tube 1 is inserted. A pair of flanges 4a and 4b and an annular groove 4c are provided in a lower end portion of the cylindrical portion 4. The annular groove 4c is located between the flanges 4a and 4b. The cylindrical portion 4 holds the test tube 1 rotatably in the circumferential direction thereof.

Figure 2:
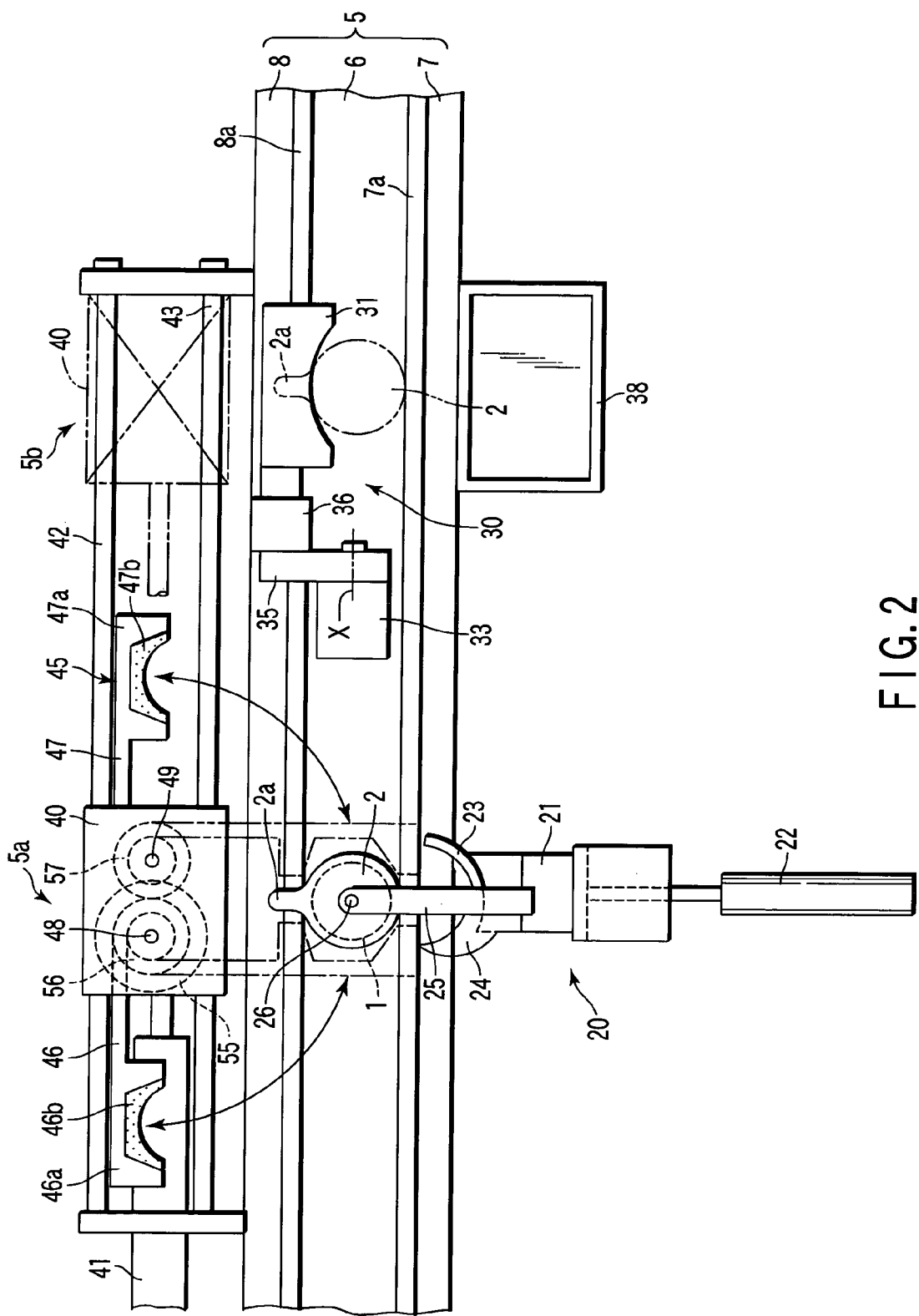
FIG. 2 is a plan view of the cap removing apparatus shown in FIG. 1.

The transfer path 5 has a belt conveyor 6 and a pair of guide rails 7 and 8. The belt conveyor 6 intermittently conveys the test tube holder 3 and the test tube 1 held therein. As shown in FIGS. 1 and 2, the guide rails 7 and 8 are arranged parallel to each other with the belt conveyor 6 interposed therebetween. The guide rails 7 and 8 respectively have guide projection lines 7a and 8a, which are engaged with the annular groove 4c of the test tube holder 3.

As shown in FIG. 2, the transfer path 5 has a first position 5a and a second position 5b, which is provided at a predetermined distance from the first position 5a. Positioning of the test tube 1 is carried out in the first position 5a. The first position 5a is hereinafter referred to as the tube-positioning position. The tube-positioning position 5a also serves as a cap-correcting position. The cap 2 is removed from the test tube 1 in the second position 5b. The second position 5b is hereinafter referred to as the cap-removing position.

In the drawings, a reference numeral 10 denotes a rotary driving mechanism. The rotary driving mechanism 10 is provided in the tube-positioning position 5a of the transfer path 5. The rotary driving mechanism 10 rotates the test tube 1 held in the test tube holder 3 in the circumferential direction.

Figure 3:
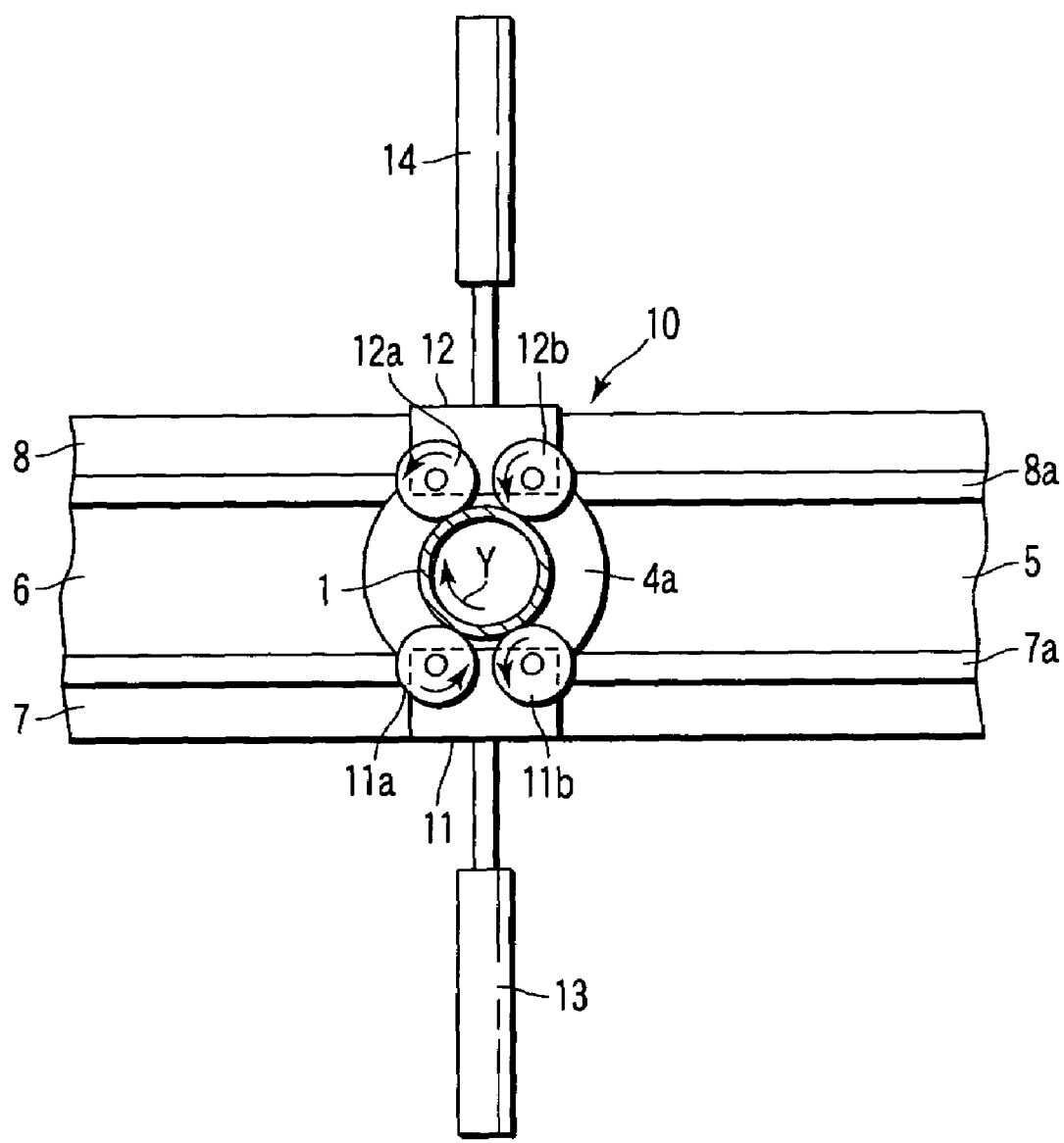
FIG. 3 is a plan view showing a state in which a test tube is clamped by a plurality of clamping rollers in the cap removing apparatus shown in FIG. 1.
Figure 4:
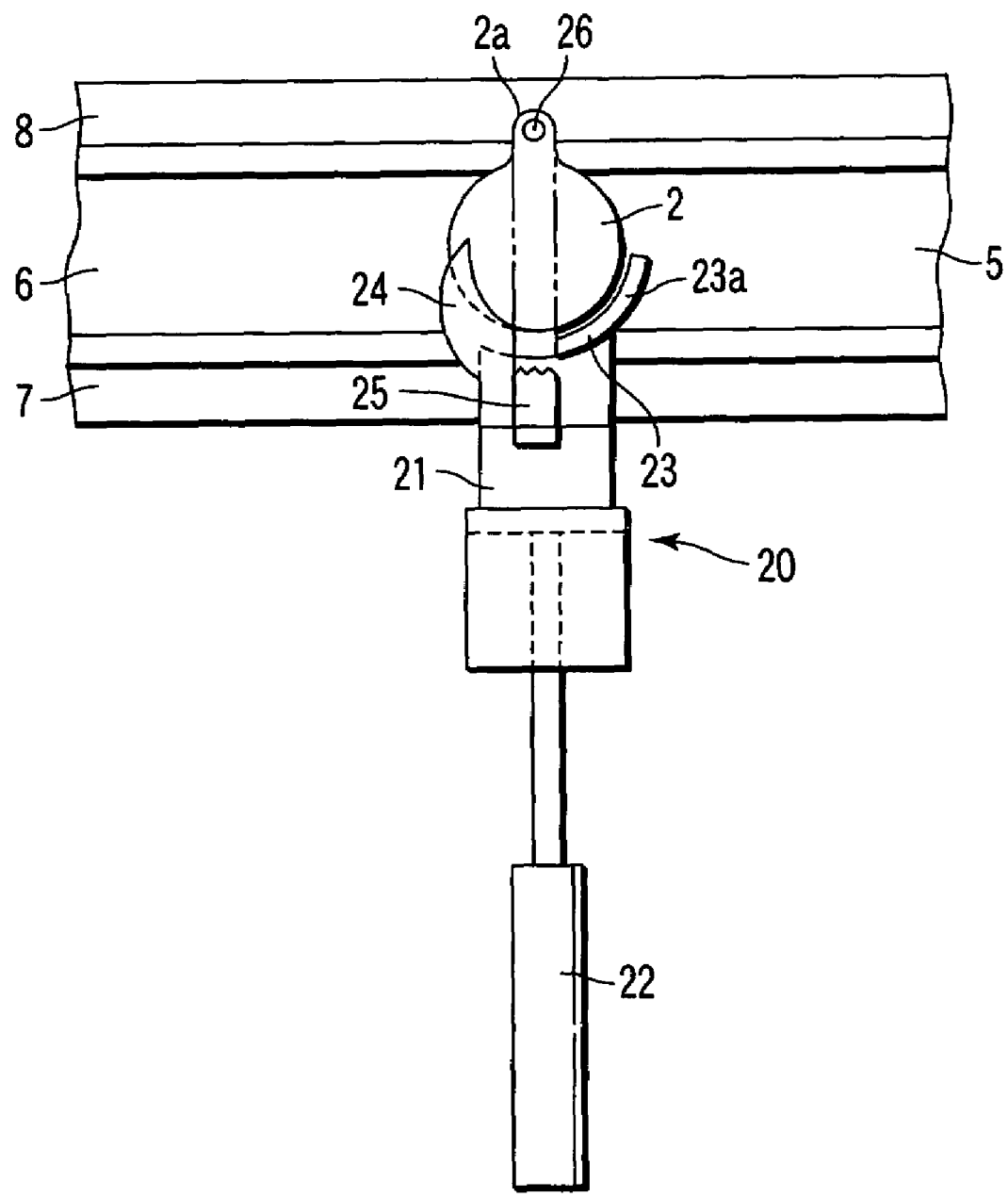
FIG. 4 is a plan view showing a correcting mechanism of the cap removing apparatus shown in FIG. 1.

As shown in FIGS. 1 and 3, the rotary driving mechanism 10 includes a pair of roller mounts 11 and 12, a pair of rollers 11a and 11b supported by one roller mount 11, a pair of rollers 12a and 12b supported by the other roller mount 12, driving motors 11c and 12c, and a pair of cylinders 13 and 14, which respectively reciprocate the roller mounts 11 and 12.

The roller mounts 11 and 12 move horizontally above the transfer path 5 by means of the cylinders 13 and 14 at right angles with the direction of transfer of the test tube 1. The rollers 11a and 11b rotate in synchronism with each other by a transmission belt (not shown). The rollers 11a and 11b are driven by the driving motor 11c. Similarly, the rollers 12a and 12b rotate in synchronism with each other by a transmission belt (not shown). The rollers 12a and 12b are driven by the driving motor 12c.

When the driving motors 11c and 12c are operated, the test tube 1 rotates in the direction Y, as shown in FIG. 3, while it is clamped by the rollers 11a, 11b, 12a and 12b.

In the drawings, a reference numeral 20 denotes a correcting mechanism. The correcting mechanism 20 corrects the posture of the knob 2a of the cap 2 closing the opening end 1a of the test tube 1. The knob 2a has flexibility. For example, the knob 2a of the cap 2 may have four shapes as shown in FIGS. 6A to 6D. The inventors configured the correcting mechanism as follows on the assumption that the knob 2a of the cap 2 may have the shapes shown in FIGS. 6A to 6D.

More specifically, the knob 2a of the cap 2 has a first posture, in which the knob 2a is bent downward relative to the horizontal (see FIG. 6A), a second posture, in which the knob 2a is bent upward, and a third posture, in which the knob 2a properly extends horizontally (see FIG. 6B). The second posture includes the two states: in the first state, the knob 2a is bent upward at an obtuse angle relative to the horizontal (see FIG. 6C); and in the second state, the knob 2a is folded upward at an acute angle relative to the horizontal (see FIG. 6D). When the knob 2a is in the third posture, it is unnecessary to correct the posture of the knob 2a.

The correcting mechanism 20 corrects all postures of the knob 2a to the third posture, which is regular posture. For this purpose, the correcting mechanism 20 has a movable metal fitting 21 movably positioned in the tube-positioning position, a cylinder 22 which moves the movable metal fitting 21, a first claw 23, which is provided on the movable metal fitting 21 and corrects the posture of the knob 2a in the first posture to the third posture (hereinafter referred to as the lower correcting claw), a second claw 24, which is provided on the movable metal fitting 21 and corrects the posture of the knob 2a in the second posture to the third posture (hereinafter referred to as the upper correcting claw), and a monitoring sensor 26 which serves as a position detecting mechanism. The monitoring sensor 26 detects the position of the knob 2a and determines the direction of the knob 2a so that the protrusion 2a can be pinched by a clamping mechanism 45 (to be described later). The lower correcting claw 23 has an inclined surface 23a, which is, for example, arc shaped. The upper correcting claw 24 extends horizontally. The top end portion of the upper correcting claw 24 is shaped like a knife edge.

As shown in FIGS. 7A to 7D, when the knob 2a of the cap 2 is in the first posture, it is guided to the inclined surface 23a and corrected to the horizontal state as shown in FIG. 6B (the third posture), as the test tube 1 rotates.

As shown in FIGS. 8A to 8D, when the knob 2a of the cap 2 is in the second posture, it is pushed by means of the top end portion of the upper correcting claw 24, and corrected to the horizontal state as shown in FIG. 6B (the third posture), as the test tube 1 rotates.

To correct the posture of the knob 2a folded upward from the test tube 1 (see FIG. 6D) by means of the upper correcting claw 24, the top end portion of the upper correcting claw 24 enters an inner part of the folded portion of the knob 2a. Then, the top end portion of the upper correcting claw 24 passes the folded portion of the knob 2a, as the test tube 1 rotates. As a result, the knob 2a is pressed downward by the upper correcting claw 24 and corrected to the horizontal state (the third posture).

As shown in FIG. 2, a support arm 25 is attached to the movable metal fitting 21. The support arm 25 extends above and across the cap 2 when the posture of the cap 2 is to be corrected. The monitoring sensor 26, which detects the presence or absence of the knob 2a, is provided at the top end of the support arm 25.

When the top end portion of the knob 2a in the third posture is located under the monitoring sensor 26, the monitoring sensor 26 detects the position. If the knob 2a is in a position where the clamping mechanism 45 (to be descried later) cannot easily pinch it, the rotation of the test tube 1 by the rotary driving mechanism 10 is stopped by a detection signal output from the monitoring sensor 26. Then, the knob 2a is moved to a position where the clamping mechanism 45 can pinch the knob 2a.

FIGS. 7A to 7C show, in sequence along a direction of rotation of the test tube 1, steps of correcting the posture of the knob 2a of the cap 2, in the case where the knob 2a is bent downward as shown in FIG. 6A. During the steps, the knob 2a of the cap 2 is guided and corrected to the third posture by means of the lower correcting claw 23. After the correction, the knob 2a is detected by the monitoring sensor 26 in the position shown in FIG. 7D. Then, the rotation of the test tube 1 is stopped. In this position, the clamping mechanism 45 (to be described later) can pinch the knob 2a, so that the cap 2 can be removed from the test tube 1.

FIGS. 8A to 8C show, in sequence along a direction of rotation of the test tube 1, steps of correcting the posture of the knob 2a of the cap 2, in the case where the knob 2a is bent upward as shown in FIGS. 6C and 6D. During the steps, the knob 2a of the cap 2 is guided and corrected to the third posture by means of the upper correcting claw 24. After the correction, the knob 2a is detected by the monitoring sensor 26 in the position shown in FIG. 8D. Then, the rotation of the test tube 1 is stopped. In this position, the clamping mechanism 45 (to be described later) can pinch the knob 2a, so that the cap 2 can be removed from the test tube 1.

As shown in FIG. 2, the cap-removing mechanism 30 is provided in the cap-removing position 5b of the transfer path 5. The cap-removing mechanism 30 pinches the knob 2a of the cap 2, whose posture has been corrected by the correcting mechanism 20, and then remove the cap 2 from the test tube 1.

Figure 5:
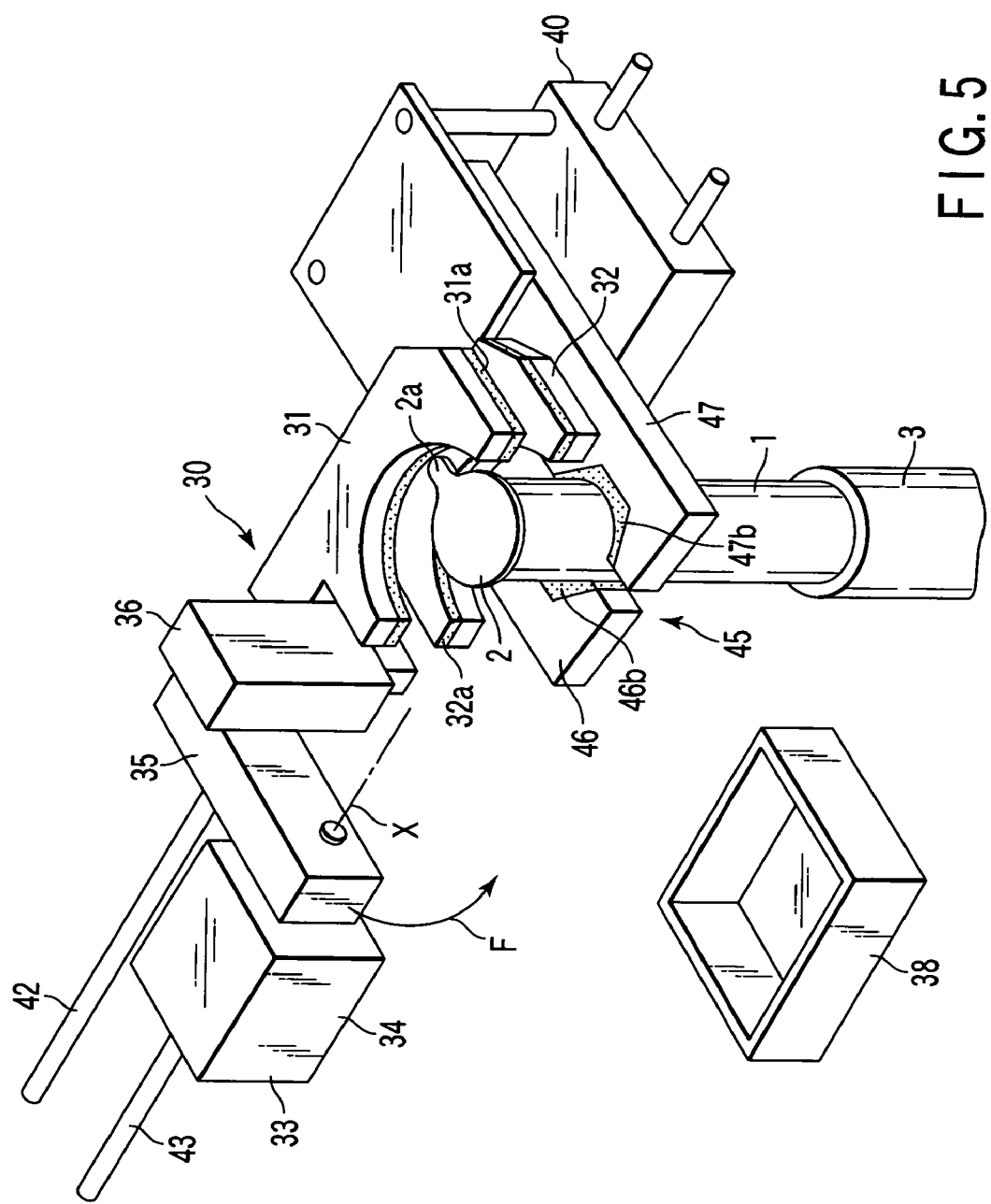
FIG. 5 is a perspective view showing the positional relationship between a cap-removing mechanism and a clamping mechanism of the cap removing apparatus shown in FIG. 1.

As shown in FIG. 5, the cap-removing mechanism 30 has an upper pinching plate 31, a lower pinching plate 32 and a rotary mechanism 33. The upper pinching plate 31 and the lower pinching plate 32 clamp the knob 2a in the cap-removing position 5b. Resilient members 31a and 32a are respectively applied to the pinching plates 31 and 32.

The rotary mechanism 33 has a rotary actuator 34 provided in the transfer path 5 and a rotary arm 35. The rotary actuator 34 is fixed, for example, above the transfer path 5. The rotary arm 35 has an operating member 36, such as a cylinder. The rotary actuator 34 operates the rotary arm 35 in a forward direction indicated by the arrow F in FIG. 5 and a reverse direction within 180 degrees around the horizontal axis X parallel to the transfer path 5.

One end of the lower pinching plate 32 is fixed to a top end portion of the rotary arm 35. The upper pinching plate 31 is moved toward or away from the lower pinching plate 32 by means of the operating member 36.

The cap-removing mechanism 30 operates as follows. The test tube 1, which is transferred through the transfer path 5, is stopped at the cap-removing position 5b. At this time, the test tube 1 is clamped by the clamping mechanism 45 (to be described later) as shown in FIG. 5. The upper pinching plate 31 and the lower pinching plate 32 pinch the knob 2a of the cap 2 of the test tube 1, which has been stopped at the cap-removing position 5b. The upper pinching plate 31 and the lower pinching plate 32 rotate in the direction of the arrow F around the horizontal axis X by the rotation of the rotary arm 35 operated by the rotary actuator 34. With the rotation of the pinching plates, the cap 2 is removed from the opening end 1a of the test tube 1.

In FIGS. 2 and 5, a reference numeral 38 denotes a collecting box. The collecting box 38 is provided under the position where the pinching plates 31 and 32 rotate. In other words, the cap 2 is removed from the test tube 1 at the position above the opening of the collecting box 38. Thus, the collecting box 38 receives the cap 2 removed from the test tube 1.

In FIGS. 1 and 2, a reference numeral 40 denotes a movable body provided in the middle of the transfer path 5. The movable body 40 is movably supported by two guide rods 42 and 43 arranged parallel to each other along the transfer path 5. The movable body 40 is reciprocated by the operation of a cylinder 41 in parallel with the transfer path 5 between the tube-positioning position 5a and the cap-removing position 5b.

The clamping mechanism 45 is mounted on the movable body 40. The clamping mechanism 45 clamps the test tube 1, when the test tube 1 is transferred to the cap-removing position 5b after the correction of the posture of the knob 2a of the cap 2. As shown in FIGS. 1, 2 and 5, the clamping mechanism 45 has a pair of clamp arms 46 and 47, a pair of gears 56 and 57, and a rotary actuator 55.

The clamp arms 46 and 47 respectively have clamping portions 46a and 47a, which clamp the test tube 1. Resilient bodies 46b and 47b are respectively attached to the clamping portions 46a and 47a. The clamp arms 46 and 47 are rotatably supported by the movable body 40 at their first ends via pivot shafts 48 and 49. The gears 56 and 57 are coaxially fixed to the pivot shafts 48 and 49 and mesh with each other. With this mesh, the clamp arms 46 and 47 rotate in synchronism with each other. The rotary actuator 55 rotates the gear 56 forward and backward, with the result that the rotation angles of the pair of clamp arms 46 and 47 are determined.

After the correction of the posture of the knob 2a, the clamping mechanism 45 clamps the test tube 1 in the tube-positioning position 5a as indicated by the imaginary lines shown in FIGS. 1 and 2. While maintaining this clamping state, the clamping mechanism 45 moves to the cap-removing position 5b together with the test tube holder 3 owing to the forward movement of the movable body 40 by the operation of the cylinder 41. In this time, the test tube holder 3 slides on the belt conveyor 6.

The clamping mechanism 45 maintains the clamping state until the removal of the cap 2 from the test tube 1 is completed, and releases the clamping state at the time when the removal is completed. Thereafter, the clamping mechanism 45 returns from the cap-removing position 5b to the tube-positioning position 5a owing to the retreat of the movable body 40 by the operation of the cylinder 41.

Because of the movable body 40 and the clamping mechanism 45 as described above, the test tube 1 whose cap 2 has been corrected can be moved from the tube-positioning position 5a to the cap-removal position 5b without changing the direction of the knob 2a determined in the tube positioning position 5a. Thus, the cap 2 can be successfully removed from the test tube 1.

Moreover, an operation between correcting the posture of the knob 2a of the cap 2 and removing the cap 2 from the test tube 1 is speeded up as compared to the conventional cap removing apparatus using a belt conveyor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cap removing apparatus comprising:
   a transfer path, which has a first position and a second position that is provided at a predetermined distance from the first position, and through which a container closed by a cap having a knob is transferred, at least a part of the container being tube-like;
   a rotary driving mechanism, which is provided in the first position and rotates the container in a circumferential direction;
   a correcting mechanism which corrects posture of the knob; and
   a cap-removing mechanism, which is provided in the second position, pinches the knob whose posture has been corrected by the correcting mechanism, and removes the cap from the container,
   wherein:
   a movable body, which is configured to move forward and backward between the first position and the second position along the transfer path, is provided on the transfer path, the movable body having a clamping mechanism; and
   the clamping mechanism clamps the container with the knob whose protrusion has been posture-corrected in the first position, moves the container from the first position to the second position by forward movement of the movable body while keeping the container in a clamping state, maintains the clamping state until removal of the cap from the container is completed, releases the clamping state at a time when the removal of the cap is completed, and returns to the first position by backward movement of the movable body.

2. The cap removing apparatus according to claim 1, wherein:
   the knob of the cap has flexibility, and the cap closes the container in a state where the knob is in a first posture, a second posture and a third posture; and
   the correcting mechanism comprises:
   a movable metal fitting arranged movably in the first position;
   a first claw, which is provided in the movable metal fitting and guides the knob by means of rotation of the container when the knob is in the first posture, thereby correcting the first posture to the third posture;
   a second claw, which is provided in the movable metal fitting and guides the knob by means of rotation of the container when the knob is in the second posture, thereby correcting the second posture to the third posture; and
   a position detecting mechanism, which detects a position of the knob and determines the direction of the knob in a direction in which the cap-removing mechanism is allowed to pinch the knob.

3. The cap removing apparatus according to claim 1, wherein the clamping mechanism comprises:
   a pair of clamp arms, respectively having clamping portions to clamp the container and rotatably supported by the movable body via pivot shafts;
   a pair of gears, fixed to the respective clamp arms so as to be coaxial with the respective pivot shafts and rotates the clamp arms in synchronism with each other; and
   a rotary actuator which rotates the clamp arms via the pair of gears.

* * * * *